United States Patent [19]

Rempfler et al.

[11] 4,016,203
[45] Apr. 5, 1977

[54] PROCESS FOR THE MANUFACTURE OF COMPOUNDS CONTAINING VINYL GROUPS

[75] Inventors: Hermann Rempfler, Binningen; Hans Bosshard; Kurt Weber, both of Basel, all of Switzerland

[73] Assignee: Ciba-Geigy Corporation, Ardsley, N.Y.

[22] Filed: June 27, 1973

[21] Appl. No.: 374,142

[30] Foreign Application Priority Data

June 30, 1972 Switzerland .................. 9852/72

[52] U.S. Cl. .................. 260/505 R; 260/240 D; 260/240.1; 260/240.9; 260/290 R; 260/308 R; 260/332.5; 8/1 W

[51] Int. Cl.$^2$ .................. C07C 143/24

[58] Field of Search ........ 260/348 R, 332.5, 505 R, 260/308 R, 290 R, 240 D, 240.1

[56] References Cited

UNITED STATES PATENTS

| | | | |
|---|---|---|---|
| 3,270,034 | 8/1966 | Greenbaum | 260/332.5 |
| 3,442,912 | 5/1969 | Hatch | 260/348 R |

FOREIGN PATENTS OR APPLICATIONS 1,228,094  4/1971  United Kingdom .............. 260/505

OTHER PUBLICATIONS

Ansell, "Supplement to the 2nd ed. of Rodd's Chemistry of Carbon Compounds" (1973), p. 277.

Primary Examiner—James O. Thomas, Jr.
Assistant Examiner—Alan Siegel
Attorney, Agent, or Firm—Karl F. Jorda; Edward McC. Roberts; Prabodh I. Almaula

[57] ABSTRACT

A novel process for the production of compounds of the formula $$A-CH=CH-D-CH=CH-A_1 \quad (I)$$

wherein A and $A_1$, independently of one another, denote phenyl, naphthyl, diphenylyl, 2-phenyl-1,2,3-triazol-4-yl or pyridyl, it being possible for A and $A_1$ to contain non-chromophoric substituents, and D denotes 4,4'-diphenylylene,1,5- or 2,6-naphthylene, or a 9,10-dihydrophenanthrene or dibenzofurane radical which is bonded to the vinylene groups in the 2,7-position, which comprises reacting in a first stage a compound of the formula $$X\text{-}CH_2\text{-}D\text{-}CH_2\text{-}X \quad (II)$$

wherein X denotes halogen, especially chlorine or bromine, hydroxyl or a group $$-O-\overset{O}{\underset{\|}{C}}-X_1,$$

wherein $X_1$ represents an aliphatic cycloaliphatic or aromatic hydrocarbon radical, especially alkyl having 1 to 6 carbon atoms, or phenyl, and D has the indicated meaning, in a strongly acid medium, in a molar ratio of at least 1:2, with an organic sulphide containing 5 to 8 ring members, of the formula $$B\overbrace{\phantom{xxx}}S \quad (III)$$

wherein B represents a polymethylene group of 4 to 7 methylene groups and wherein one of these methylene groups can be replaced by a hetero-atom and wherein these methylene groups can also contain alkyl groups with 1 to 4 carbon atoms as substituents, to give a sulphonium salt of the formula $$\left[ B\overbrace{\phantom{xx}}S^+\text{-}CH_2\text{-}D\text{-}CH_2\text{-}{}^+S\overbrace{\phantom{xx}}B \right] 2\frac{M^{n-}}{n} \quad (IV)$$

wherein M represents the anion of the strong acid used and $n$ denotes the numbers 1 or 2; reacting, in a second stage, the resulting sulphonium salt with 2 mols of an aldehyde of the formula (V) A-CHO or (VI) $A_1$-CHO or their mixture, in the presence of strong bases, in a strongly polar, protic or aprotic, water-miscible solvent to give a diepoxide of the formula $$A-\underset{O}{\underset{\diagdown\diagup}{CH\text{-}CH}}-D-\underset{O}{\underset{\diagdown\diagup}{CH\text{-}CH}}-A_1 \quad (VII)$$

and subjecting in a 3rd stage, the diepoxide of the formula (VII), thus obtained, to a reduction according to processes which are in themselves known for the reduction of epoxides, with elimination of the epoxide oxygen and formation of vinylene groups.

11 Claims, No Drawings

PROCESS FOR THE MANUFACTURE OF COMPOUNDS CONTAINING VINYL GROUPS

The present application relates in a first aspect, to a process for the manufacture of compounds containing vinyl groups, which can be used as optical brighteners and which belong to the group of the diphenyls, naphthalenes, dihydrophenanthrenes and dibenzofuranes which are substituted by triazolylvinyl radicals or styryl radicals.

Whilst some processes for the manufacture of compounds of the abovementioned types are already known, they are either processes which for economic reasons can hardly be considered for industrial exploitation or they are processes which only permit the manufacture of certain special groups of compounds or they are processes which suffer from the fact that by-products which cannot be utilised further are produced.

The process according to the present invention overcomes these disadvantages in that it is not only capable of broad use but also operates economically and without undesired by-products.

The subject of the invention is a process for the manufacture of compounds which serve as optical brighteners and correspond to the formula $$A-CH=CH-D-CH=CH-A_1 \qquad (I)$$

wherein A and $A_1$ independently of one another denote phenyl, naphthyl, diphenylyl, 2-phenyl-1,2,3-triazol-4-yl or pyridyl, it being possible for A and $A_1$ to contain non-chromophoric substituents, and D denotes the 4,4'-diphenylylene radical, 1,5- or 2,6-naphthylene radical or a 9,10-dihydrophenanthrene or dibenzofurane radical which is bonded to the ethylene groups in the 2,7-position. This process is characterised in that in a first stage a compound of the formula $$X-CH_2-D-CH_2-X \qquad (II)$$

wherein X denotes a halogen atom, especially chlorine or bromine, the hydroxyl group or a group

wherein $X_1$ represents an aliphatic, cycloaliphatic or aromatic hydrocarbon radical, especially an alkyl radical with 1 to 6 carbon atoms, or the phenyl radical, and D has the indicated meaning, is reacted in a strongly acid medium, in a molar ratio of at least 1:2, with an organic sulphide containing 5 to 8 ring members, of the formula

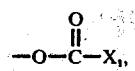 (III)

wherein B represents a polymethylene group of 4 to 7 methylene groups and wherein one of these methylene groups can be replaced by a hetero-atom and wherein these methylene groups can also contain alkyl groups with 1 to 4 carbon atoms as substituents, to give a sulphonium salt of the formula

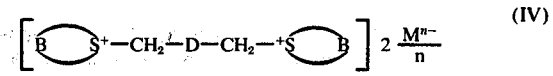

wherein M represents the anion of the strong acid used and $n$ denotes the numbers 1 or 2; that, further, in a second stage the resulting sulphonium salt is reacted with 2 mols of an aldehyde of the formula $$A\text{-CHO} \qquad (V)$$
or
$$A_1\text{-CHO} \qquad (VI)$$

or their mixture, in the presence of strong bases, in a strongly polar, protic or aprotic, water-miscible solvent to give a diepoxide of the formula

and that the diepoxide of the formula (VII), thus obtained, is subjected, in a 3rd stage, to a reduction according to processes which are in themselves known for the reduction of epoxides, with elimination of the epoxide oxygen and formation of ethylene groups.

Possible non-chromophoric substituents of the radicals A and $A_1$ are above all alkyl with 1 to 18, preferably 1 to 4, carbon atoms, for example methyl, ethyl or tert.-butyl, alkoxy with 1 to 18, preferably 1 to 4, carbon atoms, for example, methoxy, cycloalkyl, preferably cyclohexyl, halogen, preferably fluorine and chlorine, trifluoromethyl, the nitrile group, sulphone groups, the sulphonic acid group as well as its salts, esters or amides, and the carboxylic acid group as well as its salts, esters or amides.

Amongst the sulphone groups there are to be mentioned the arylsulphones and aralkylsulphones, such as phenylsulphone and benzylsulphone, and also, above all, alkylsulphones with 1 to 4 carbon atoms, for example methylsulphone.

Whilst in the case of the sulphonic acid esters and carboxylic acid esters of aromatic or araliphatic nature the phenyl esters (optionally substituted, for example by chlorine, methyl or methoxy) and benzyl esters are of practical interest, in the case of the aliphatic esters the cyclohexyl ester and, above all, alkyl esters with 1 to 18, preferably 1 to 4, carbon atoms are used.

By the amides of the sulphonic acid group or of the carboxylic acid group there are to be understood, alongside the unsubstituted amide, also the monosubstituted and disubstituted representatives, and the substituting component can be of aromatic (anilide), araliphatic or cycloaliphatic nature and also, in particular, of aliphatic nature. Aliphatic members generally have 1 to 18, preferably 1 to 4, carbon atoms. By disubstituted amides there are also to be understood amides in which the amide nitrogen atom represents a ring member of a heterocyclic structure such as, for example, of the morpholino, piperidino, pyrrolidino or hexamethyleneimino radical.

In the case of the salts of the sulphonic acid and carboxylic acid group, the water-soluble types such as the alkali metal salts, preferably the sodium or potassium salts, ammonium salts or amine salts are of practical interest; on the other hand, this is not intended to exclude from the invention other salts such as, for example, barium or calcium salts.

Within the scope of the formula (I), symmetrical compounds, that is to say those in which $A_1$ and A are identical, are of particular interest.

In the formula (I) the symbols A and $A_1$ preferably represent non-chromophorically substituted phenyl or 2-phenyl-1,2,3-triazol-4-yl radicals. The symbol D preferably denotes the 4,4'-diphenylylene or the 2,7-dibenzofurane radical.

Compounds within the scope of the formula (I) which are particularly easily accessible according to the process of the invention are those of the formula

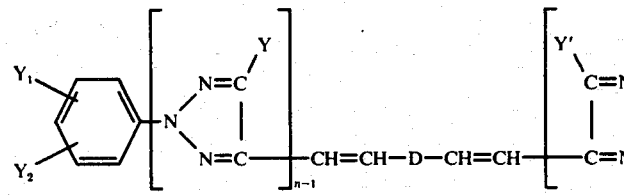
(VIII)

wherein Y and Y' independently of one another denote hydrogen or methyl, $Y_1$ and $Y_1'$ independently of one another denote hydrogen, the sulphonic acid group or its Na, K or ammonium salt, carbomethoxy, nitrile or methoxy, $Y_2$ and $Y_2'$ independently of one another denote hydrogen, chlorine, methyl or the sulphonic acid group or its Na, K or ammonium salt, n and m independently of one another denote the number 1 or 2 and D denotes the 4,4'-diphenylylene radical, the 1,5- or 2,6-naphthylene radical or a 9,10-dihydrophenanthrene or dibenzofurane radical which is bonded to the ethylene groups in the 2,7-position, and of the formula

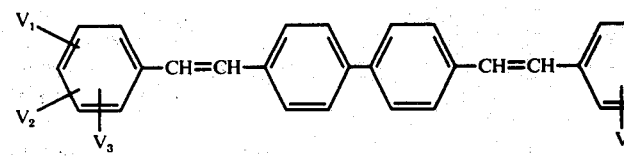
(IX)

wherein $V_1$ and $V_1'$ independently of one another denote hydrogen, a sulphonic acid group as well as its salts, esters or amides, a carboxylic acid group as well as its salts, esters or amides, the nitrile group, a sulphone group or a methyl group, $V_2$ and $V_2'$ independently of one another denote hydrogen, an alkyl group containing 1 to 18 carbon atoms, an alkoxy group containing 1 to 12 carbon atoms, halogen or a sulphonic acid group, as well as its salts, esters or amides and $V_3$ and $V_3'$ independently of one another denote hydrogen, halogen or an alkyl group containing 1 to 4 carbon atoms, as well as compounds of the formula

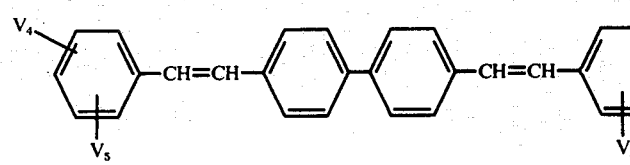
(X)

wherein $V_4$ denotes hydrogen, a sulphonic acid group as well as its salts, esters or amides, a carboxylic acid group as well as its salts, esters or amides, halogen or the nitrile group and $V_5$ denotes hydrogen, halogen, a sulphonic acid group as well as its salts, esters or amides, an alkyl group with 1 to 4 carbon atoms or an alkoxy group with 1 to 4 carbon atoms.

Appropriately, to manufacture these compounds (according to the process defined above) a compound of the formula

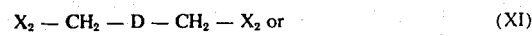
$$X_2 - CH_2 - D - CH_2 - X_2 \text{ or} \qquad (XI)$$

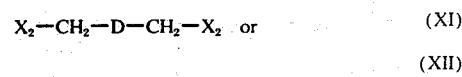
$$X_2 - CH_2 - D - CH_2 - X_2 \text{ or} \qquad (XI)$$
$$\qquad (XII)$$

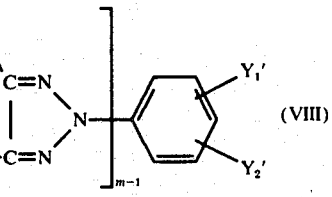

wherein $X_2$ represents chlorine or bromine is employed in the first process stage and the sulphonium salt manufactured therefrom is reacted, in a second process stage, with aldehydes of the formulae

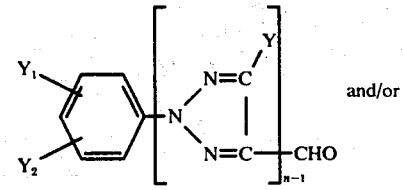
and/or
(XIII)

-continued

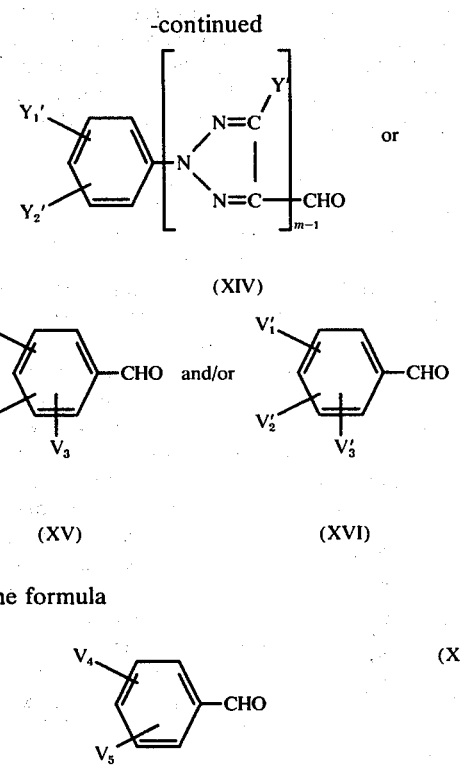

or of the formula

In general, compounds of the formula (II) employed in the first stage in the process according to the invention are those in which X denotes chlorine or bromine, that is to say 4,4'-bis-(chloromethyl)-diphenyl, 4,4'-bis-(bromomethyl)-diphenyl, 1,5- or 2,6-bis-(chloromethyl)-naphthalene, 1,5- or 2,6-bis-(bromomethyl)-naphthalene, 2,7-bis-(chloromethyl)-9,10-dihydrophenanthrene, 2,7-di-(bromomethyl)-9,10-dihydrophenanthrene and 2,7-bis-(bromomethyl)-dibenzofurane.

Examples of organic sulphides of the formula (III) to be used in the 1st stage are: tetrahydrothiophene, 2- or 3-methyl-tetrahydrothiophene, 3-ethyl-tetrahydrothiophene, 2,4-dimethyl-tetrahydrothiophene, 2,3-dimethyl-tetrahydrothiophene, thiacyclohexane, thiacycloheptane, 1,3- or 1,4-dithiacyclohexane and 1,4-oxathiacyclohexane.

Amongst these, 1,4-oxathiacyclohexane, thiacyclohexane, thiacycloheptane and especially tetrahydrothiophene are preferred.

Though mixtures of organic sulphides of the formula (III) can also be employed in the process according to the invention, preferably at least 2 mols of only one sulphide of the formula (III) are employed.

The reaction of the reactants of the 1st stage in a strongly acid medium is appropriately carried out at temperatures of about −20° C to 120° C, preferably at 40° to 70° C.

Inorganic acids, especially hydrochloric acid, hydrobromic acid, hydrofluoric acid, perchloric acid, sulphuric acid or phosphoric acid, are advantageously used to form the strongly acid medium. These acids are preferably employed in the aqueous form; however, it is also possible to use solutions of anhydrous inorganic acids in organic solvents which are inert under the reaction conditions, for example lower aliphatic alcohols, such as methanol and ethanol, acetic acid, propionic acid, acetic anhydride, sulpholane, dioxane, nitromethane, benzene, chlorobenzene, nitrobenzene or nitrotoluene or a mixture of such solvents. Aqueous sulphuric acid, especially 60 to 80% strength aqueous sulphuric acid, or aqueous hydrochloric acid, especially 35 to 38% strength aqueous hydrochloric acid, are particularly preferred as the strongly acid medium.

According to the definition, the compounds of the formula (II) and the organic sulphides of the formula (III) are employed in a molar ratio of at least 1:2; however it is advisable to work with an approximately 5 to 30% excess of organic sulphide.

The acid must also be present in at least equivalent amount but preferably an excess of acid is used.

In practice, the reaction according to the invention can be carried out by mixing the compound of the formula (II) with the organic sulphide of the formula (III) and introducing the mixture into the acid medium. It is, however, also possible initially to introduce the compound of the formula (II) into the acid medium and to add the organic sulphide subsequently or, finally and preferably, to introduce the organic sulphide initially into the acid medium and then to add the compound of the formula (II). The reaction time is generally 1 to 50 hours, depending on the reactivity of the components.

The isolation and working up of the sulphonium salts of the formula (IV) can be effected in various ways, depending on the reaction medium and on the solubility properties of the end product. If volatile inorganic acids, such as hydrochloric acid, are used, the reaction products can, especially when working in an anhydrous medium, be separated off directly or be isolated, for example, by evaporation under reduced pressure. The sulphonium salts can also be precipitated by diluting the acid aqueous reaction medium with a suitable water-miscible organic solvent in which the sulphonium salt is insoluble, such as acetone, and be filtered off subsequently. Finally, the reaction medium can, in the case of the reaction in aqueous sulphuric acid or aqueous phosphoric acid, be neutralised with calcium hydroxide after dilution with ice water; after separating off the calcium sulphate or calcium phosphate which has separated out, the aqueous solution is evaporated in vacuo.

In accordance with their salt character, the sulphonium salts manufactured according to the new process in the 1st stage are solid substances. At elevated temperatures some of them melt in an ill-defined manner, with decomposition. They are characterised, for example, as the halide, especially chloride, and also as the bisulphate, sulphate, perchlorate, thiocyanate, picrate or picrylsulphonate but, because of their low solubility, especially as the Reineckate. Most sulphonium salts are very readily water-soluble in the form of their halides and sulphates; frequently, however, they also dissolve in organic solvents, such as ethanol or chloroform.

The method hitherto generally employed for the manufacture of sulphonium salts consisted of the alkylation of thioethers in a non-acid medium (compare USP 2,794,026, USP 3,078,259 and USP 3,455,967). In many cases, however, the yield thereof was relatively low or no reaction at all occurred. It was also frequently necessary to use as alkylating agents the expensive alkyliodides which are frequently only accessible with difficulty. In contrast, the process according to the invention described above permits the manufacture of sulphonium salts in an economical manner and in good yields.

For the conversion of the sulphonium salt of the formula (IV) into the bis-epoxide compound of the formula (VII), which takes place in the second stage, the sulphonium salt, in a strongly polar protic or aprotic water-miscible solvent, is first treated with a strong base and the aldehyde of the formula (V), or a mixture of the aldehydes of the formulae (V) and (VI), preferably first adding the base and then the aldehyde or the aldehyde mixture to the sulphonium compound dissolved in the solvent. Polar protic or aprotic solvents employed are, for example, dimethylformamide or isopropanol, but above all primary aliphatic alcohols, such as methanol, ethanol and methylcellosolve. A mixture of such a solvent with water is also a suitable reaction medium in many cases. The latter is in particular unavoidable if the reaction mixture arising in the 1st stage is passed directly, without isolation of the sulphonium compound, to the secondary reaction stage. The proportion by weight of water can be up to 50% but is preferably not more than 30%. At least two mols of base are required per mol of sulphonium salt. In general, an excess of base of 5 to 20% is used. The bases used are preferably KOH or NaOH which can be employed as concentrated aqueous solutions. If the reaction mixture coming from the 1st reaction stage is used without isolation of the sulphonium compound it is, of course, necessary to employ, additionally to the amount of base mentioned, the base required to neutralise the excess acid. The sulphonium salt, the base and the aldehyde or the aldehyde mixture must be brought together at temperatures below 20° C, for example at −40° C. It is advantageous to keep the temperature of the reaction mixture below −5° C during this operation and industrially temperatures of down to −20° C are above all of interest. After the sulphonium salt, the strong base and the aldehyde or the aldehyde mixture have been mixed with one another, the temperature of the reaction mixture is raised, it being possible to warm the mixture as far as the boiling point of the solvent, but preferably to temperatures between 40° and 80° C.

In general, however, the reaction mixture is warmed to temperatures of 20° to 80° C, preferably 40° to 70° C, the upper limit being determined by the boiling point of the solvent.

Examples of aldehydes to be used in this 2nd reaction stage are: Benzaldehyde, pyridinealdehyde-(2), pyridine-aldehyde-(4), 2-sulphobenzaldehyde, 4-sulphobenzaldehyde, 2,4-disulphobenzaldehyde, 2,5-disulphobenzaldehyde, 2-chlorobenzaldehyde, 2-methylbenzaldehyde, 4-carbomethoxybenzaldehyde, 3-sulpho-4-chlorobenzaldehyde, 2-sulpho-4-cyanobenzaldehyde, 2-sulpho-4-carboxybenzaldehyde, 3-sulphobenzaldehyde, 3-sulpho-4-methoxybenzaldehyde, 3-sulpho-4-methylbenzaldehyde, 4-methylbenzaldehyde, 4-cyanobenzaldehyde, 2,4,5-trimethylbenzaldehyde, 4-carboxybenzaldehyde, 2-cyanobenzaldehyde, 2,4-dichlorobenzaldehyde, 4-phenylbenzaldehyde, 4-methyl-sulphonylbenzaldehyde, 3-chlorobenzaldehyde and 3-methoxybenzaldehyde.

The compounds of the formulae (II), (III), (V) and (VI) which can be used as starting substances according to the invention are known or can be manufactured according to known methods.

The diepoxides are isolated by means of customary methods, such as concentration, or evaporation of the solvent, precipitation with a suitable solvent, salting out and the like. The choice of the method depends above all on the nature of the substituents in A and $A_1$. In certain cases it is not necessary to isolate the diepoxide from the reaction mixture before reducing it to the compound of the formula (I), since the reduction can particularly be carried out in the medium which is already present.

The reduction of the diepoxides of the formula (VII) to the compounds of the formula (I), to be carried out in the 3rd stage, takes place according to methods which are in themselves known.

A preferred method is, for example, reduction with thiourea. For this, the bis-epoxide compound and the thiourea are brought together in a suitable solvent, the reaction mixture generally being warmed to temperatures which lie between 20° C and the boiling point of the solvent. Suitable solvents are above all polar solvents, such as water, methanol, ethanol, methylcellosolve, dimethylformamide or mixtures of these solvents, such as, say, methanol/water or dimethylformamide/water. Suitable solvents for the reduction of diepoxides free of sulpho groups are, in particular, methylcellosolve or dimethylformamide whilst suitable solvents for the reduction of diepoxides containing sulpho groups are water or methanol. Per mol of diepoxide to be reduced, (of course) at least 2 mols of thiourea are required. To achieve as complete reduction as possible, it is, however, also possible to employ an excess of thiourea, which preferably amounts to up to 50%. The diepoxides can also be reduced with thiocyanates, under the same conditions as with thiourea, to give compounds of the formula (I).

A further method which is in itself known is the reduction by means of zinc and sodium hydroxide solution or zinc and acetic acid which is carried out, for example, in water and methanol or dimethylformamide, at 20° to 100° C.

Furthermore, the reduction of the diepoxides can also be carried out catalytically with hydrogen in a manner which is in itself known, catalysts used being above all platinum, palladium or, especially, Raney nickel.

EXAMPLE 1

25.1 g of 4,4′-bis-(chloromethyl)-diphenyl and 21.2 g of tetrahydrothiophene are introduced into 25 ml of 37% strength aqueous hydrochloric acid. The reaction mixture is kept at a temperature of 65° C for 4 hours, whilst stirring and is subsequently cooled to approx. 20° C and mixed with 250 ml of acetone. The reaction product is then caused to crystallise through cooling with ice and is filtered off and dried in vacuo at room temperature (approx. 25°). 50.2 g of a white, crystalline, chromatographically pure product of the formula

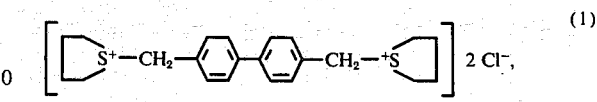

(1)

are obtained, which still contains solvent of crystallisation and has a melting point of 104 to 105° C. Taking into account the analytically determined purity, the yield is found to be 98% of theory.

The purity is determined by precipitating an aliquot part of the sulphonium salt with an aqueous Reinecke salt solution. The resulting sparingly soluble Reineckate of melting point 185° C is dried and weighed.

Instead of isolating the end product by diluting the reaction mixture with an acetone, it is also possible to work up the mixture by distilling off the hydrochloric acid and the excess tetrahydrothiophene under reduced pressure.

If in the above examples, whilst otherwise following the same procedure, 25 ml of 37% strength aqueous hydrochloric acid are replaced by the corresponding volume of water, 36% of theory of a non-crystalline smeary mixture consisting of mono- and bis-sulphonium compound are obtained.

The table which follows lists further sulphonium salts which have been manufactured according to the process described above. Herein Reineckate denotes the salt with the anion $[Cr(SCN)_4(NH_3)_2]^-$.

addition, the reaction mixture is stirred for a further 3 hours at 60° C. The resulting sulphur is filtered off and the filtrate is treated with 80 g of sodium chloride added in portions at 60° C. After slowly cooling to 5° C, the precipitate is filtered off and dried for 10 hours in vacuo at 70° C. 31.4 g of a product are obtained, of which the content of compound of the formula

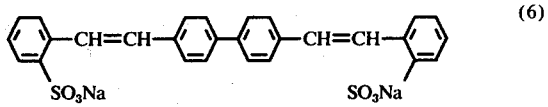

(6)

as determined by UV spectroscopy is found to be 55%, by comparison with the pure product. This corresponds to a yield of 61% of (6). The residual content consists of water of hydration and sodium chloride. The pure

Table

| Compound of the formula (II) | Sulphide | Reaction conditions, hrs/° C | Acid medium | Sulphonium salt of the formula | Yield, % of theory (chloride) | Melting point |
|---|---|---|---|---|---|---|
| ClCH₂—⟨◯⟩—⟨◯⟩—CH₂Cl | ⟨S⟩ (thiophene) | 9 hrs/60° | Aqueous 35% strength HCl | [⟨S⟩—⁺CH₂—⟨◯⟩—⟨◯⟩—CH₂—⁺S⟨⟩] 2 Cl⁻ (2) | 95% | Reineckate 197° (decomposition) |
| " | ⟨S⟩ | 16 hrs/60° | " | [⟨S⟩—⁺CH₂—⟨◯⟩—⟨◯⟩—CH₂—⁺S⟨⟩] 2 Cl⁻ (3) | 55% | Reineckate 163° (decomposition) |
| " | ⟨S O⟩ | 24 hrs/60° | " | [⟨O S⟩—⁺CH₂—⟨◯⟩—⟨◯⟩—CH₂—⁺S⟨O⟩] 2 Cl⁻ (4) | 58% | Reineckate 161° (decomposition) |

21.4 g of the bis-sulphonium compound of the formula (1) are dissolved in 200 ml of methanol. 6 g of NaOH, dissolved in 10 ml of water, are added dropwise to the solution at −10° to −15° C. After the addition of 23 g of the Na salt of benzaldehyde-2-sulphonic acid, the solution is warmed to 60° C and stirred at this temperature for 2 hours. Thereafter the solvent is evaporated off. The resulting tetrahydrothiophene distils over with the methanol and can be recovered almost quantitatively. The residue is recrystallised from water and dried in vacuo over $P_2O_5$. 24.1 g (80% of theory) of the compound of the formula

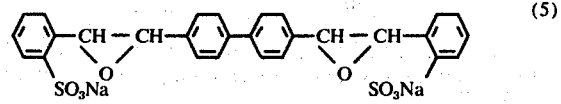

(5)

are obtained.

29.5 g of the bis-epoxide of the formula (5) are dissolved in 150 ml of water at 60° C and the solution is adjusted to pH 8 with sodium carbonate solution. 8.4 g of thiourea, dissolved in 80 ml of $H_2O$, are then added dropwise over the course of 1 hour. After the dropwise product obtained by repeated recrystallisation from water and by drying in a high vacuum at 120° C shows a molar extinction of 71,000 at $\lambda_{max}$ 353 nm.

The sulphonium salts of the formulae (2) to (4) can be reacted analogously to give the compound of the formula (6).

EXAMPLE 2

10 g of the bis-epoxide of the formula (5) obtained according to Example 1 are dissolved in 150 ml of water and the solution is heated to 30° − 40° C. After the addition of Raney nickel as the catalyst, hydrogenation is carried out for 32 hours under normal pressure. A little n-amyl alcohol can be added to de-foam the solution. After completion of the hydrogenation, the catalyst is filtered off and the solvent is evaporated. 9.5 g of a product are thus obtained, of which the content of compound of the formula (6) is determined as 60% by UV-spectroscopy, as described in Example 1.

EXAMPLE 3

50.2 g of 4,4'-bis-(chloromethyl)-biphenyl and 42.2 g of tetrahydrothiophene are introduced into 50 ml of 37% strength aqueous hydrochloric acid. The suspension is warmed and stirred for 4 hours at 65° C. The solution is poured into 500 ml of methanol and the mixture is cooled to between −10 and −15° C. 140 g of 30% strength aqueous sodium hydroxide solution are added dropwise at this temperature, whilst stirring vigorously, and thereafter 91.5 g of benzaldehyde-2-sulphonic acid are added. The suspension is warmed and stirred for 2 hours at 60° C. The resulting tetrahydrothiophene is distilled off with the methanol, on a rotary evaporator, almost to dryness. After adding 150 ml of water, the mixture is again evaporated almost to dryness. The residue is dissolved in 550 ml of water at 60° C. After adding 135 g of sodium chloride in small portions, the mixture is slowly cooled to 5° C and the precipitate is filtered off and eluted with 25% strength aqueous sodium chloride solution. After drying in vacuo at 70° C for 14 hours, 110.3 g (92.7% of theory) of the product of the formula

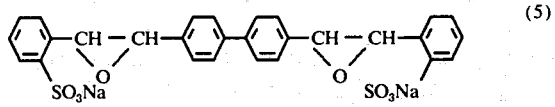

(5)

are obtained; this is converted into the compound of the formula (6) as described in Example 1.

EXAMPLE 4

21.4 g of 4,4'-bis-(methylene-thiophanium)-biphenyl dichloride, manufactured according to Example 1, are dissolved in 200 ml of methanol and the solution is cooled to −7° C. 6.1 g of sodium hydroxide (98% purity) dissolved in 10 ml of water are then slowly added dropwise over the course of one hour at −5 to −10° C, whilst stirring. 16.0 g of 2-chlorobenzaldehyde are then added, in the course of which the temperature rises to 15° C. The mixture is stirred for a further hour at 15° to 20° C, heated to 60° C over the course of 20 minutes and stirred for a further hour at this temperature. The reaction mixture is evaporated to dryness on a rotary evaporator, the residue is suspended in a mixture of 100 ml of ethanol and 100 ml of water and the product is filtered off, washed with 500 ml of water and dried in vacuo at 60° to 65° C. 16.7 g (72.8% of theory) of the stereoisomer mixture of the compound of the formula

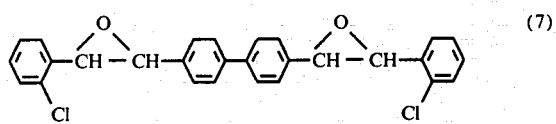

(7)

are thus obtained as a white powder. Melting range 132° to 137° C.

Recrystallisation from 100 ml of tetrachloroethylene with the aid of fuller's earth, gives 2.5 g of a pure stereoisomer as a white powder of melting point 158° to 160° C.

EXAMPLE 5

24.8 g of 4,4'-bis-(methylene-thiophanium)-diphenyl dichloride (86.0% purity) are dissolved in 200 ml of methanol and the solution is cooled to −10° C. 6.1 g of sodium hydroxide (98% purity) dissolved in 10 ml of water are then added dropwise over the course of 1 hour at −10° C, whilst stirring. 12.2 g of benzaldehyde (96% purity) are then added. After 1½ hours the temperature has risen to 18° C. The mixture is stirred for a further 1½ hours at 18° to 21° C and then for 1 hour at 60 to 65° C. After cooling to room temperature, 200 ml of water are added and the product is filtered off, washed with water and dried in vacuo at 60° to 65° C. 14.8 g (75.9% of theory) of a stereoisomer mixture of the compound of the formula

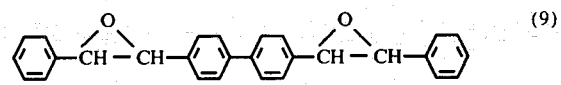

(9)

are thus obtained as a white powder; melting range: 183° to 195° C.

Recrystallisation from 150 ml of tetrachloroethylene yields 5.3 g of the compound of the formula (9) of melting point 202° to 212° C (stereoisomer mixture).

7.8 g of the bis-epoxide of the formula (9) are suspended in 150 ml of methylcellosolve and 20 ml of benzene. After adding 3.4 g of thiourea, the mixture is heated to 80° C. After 20 hours' reaction time, the reaction mixture is cooled and the precipitate is filtered off. The latter is extracted with benzene in order to separate off unreacted bis-epoxide. The sparingly soluble bis-stilbene of the formula

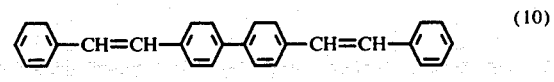

(10)

is left; it has a melting point of 328° to 330° C.

The following epoxides of the formula

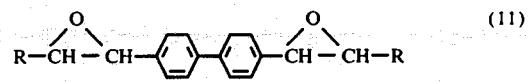

(11)

are obtained analogously to the above description.

| Formulae | R | Yield, % of theory | Melting point °C |
|---|---|---|---|
| (12) | ![phenyl] | 75.1 | 175 – 184 [1] |
| (13) | ![methylphenyl with CH₃] | 83.5 | 198 – 208 [2] |
| (14) | ![phenyl-COOCH₃] | 91 | 140 – 165 |
|  | ![phenyl-OCH₃] |  |  |

[1] After recrystallisation from 100 ml of tetrachloroethylene the melting point was 194 to 200° C.
[2] After recrystallisation from 180 ml of chlorobenzene, the melting point was 214 to 218° C.

Reduction of the epoxides of the formulae (7), (12), (13) and (14) by means of thiourea, in accordance with the method described above, yields the compounds of the formulae

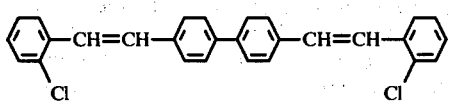

(15)

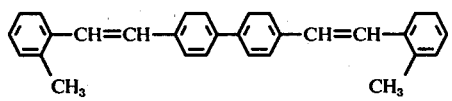

(16)

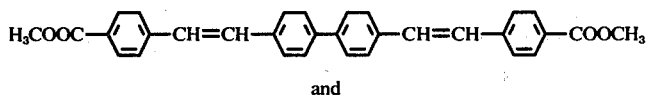

(17)

and

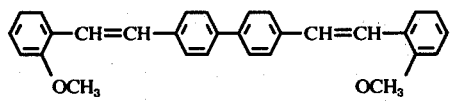

(18)

EXAMPLE 6

6 g of the bis-epoxide of the formula (9) manufactured according to Example 5 are dissolved in 300 ml of tetrahydrofurane. After adding 0.5 g of Pd-BaCO$_3$, 5% strength, as the catalyst, hydrogenation is carried out under normal pressure at 20°–25° C. After the theoretical amount of hydrogen has been taken up, the catalyst is filtered off, the filtrate is evaporated and the residue is recrystallised from toluene. 5.2 g (86% of theory) of the product of the formula

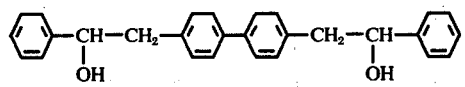

(19)

are thus obtained as colourless crystals of melting point 177°–179° C.

5 g of the product of the formula (19) are dissolved in 350 ml of hot toluene and after adding 0.1 g of p-toluenesulphonic acid the mixture is heated under reflux for 2 hours. 300 ml of toluene are then distilled off. The reaction solution which remains is filtered hot and the residue is rinsed with a little hot methanol. 4.2 g (93% of theory) of the bistilbene of the formula (10) are thus obtained.

EXAMPLE 7

15.9 g of 2,7-bis-(bromomethyl)-dibenzofurane and 11.9 g of tetrahydrothiophene are introduced into 60 ml of 37% strength hydrochloric acid. The reaction mixture is stirred for 6 hours at 60° C. The hydrochloric acid is evaporated off in vacuo and the residue is taken up in a little ethanol. Hereupon, crystallisation immediately occurs and is completed by ice cooling. The product is filtered off and dried in vacuo at room temperature. 19.8 g (83% of theory) of the white, chromatographically pure product of the formula

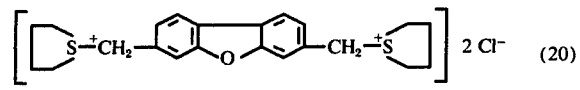

2 Cl$^-$ (20)

of melting point 191° to 194° C are obtained.

6.6 g of the bis-sulphonium compound of the formula (20) are suspended in 100 ml of methanol. 1.8 g of NaOH, dissolved in 3 ml of H$_2$O, are added dropwise at −10° C. After addition of 3.5 g of benzaldehyde, the suspension is stirred for 3 hours at room temperature and then for 1 hour at 60° C. The reaction mixture is cooled to room temperature and the precipitate is filtered off and eluted with a little methanol. Recrystallisation from cyclohexane, and drying, gives 2.6 g (43% of theory) of the compound of the formula

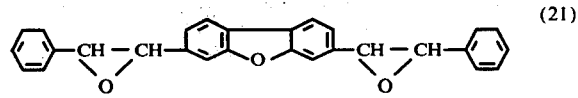

(21)

of melting point 165° to 170° C.

2 g of the bis-epoxide of the formula (21) are dissolved in 100 ml of tetrahydrofurane at 40° C. After adding palladium as the catalyst, hydrogenation is carried out under normal pressure until the theoretical amount of H$_2$ has been taken up. The catalyst is filtered off and the filtrate is evaporated. Recrystallisation from cyclohexane gives 1.4 g (70% of theory) of the product of the formula

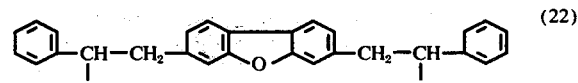

(22)

of melting point 129° C.

10 g of substance of the formula (22) in 500 ml of toluene and 500 mg of p-toluenesulphonic acid as the catalyst are heated for 2 hours under reflux. 400 ml of toluene are distilled off. The yellow crystals are filtered off, washed with a little CHCl$_3$ and dried. 8.0 g (88% of theory) of the compound of the formula

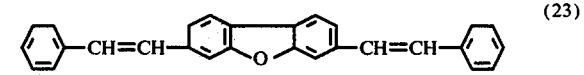

(23)

of melting point 279° to 281° C are thus obtained.

EXAMPLE 8

6.6 g of bis-sulphonium compound of the formula (20) are suspended in 100 ml of methanol. 1.8 g of NaOH, dissolved in 3 ml of H$_2$O, are added dropwise at −10° C. After adding 8.4 g of the Na salt of benzaldehyde-2-sulphonic acid, the mixture is stirred for 3 hours at room temperature and then for ½ hour at 60° C. After filtering off the by-product, the filtrate is concentrated on a rotary evaporator. The residue, in 50 ml of water, is warmed to 60° C. 5.1 g (56% of theory) of the product of the formula

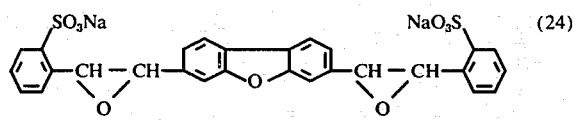

can be salted out by slowly adding 12 g of NaCl, whilst stirring, and subsequently cooling the mixture.

Reduction of the compound of the formula (24) according to the method described in Example 1 by means of thiourea yields the compound of the formula

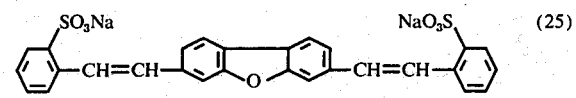

EXAMPLE 9

5.3 g of bis-sulphonium compound of the formula (1) are dissolved in 50 ml of methylcellosolve. 1.5 g of NaOH, dissolved in 6 ml of water, are added dropwise to the solution at −10° C. The resulting sodium chloride is filtered off and 9.3 g of di-Na salt of 2,4-disulphobenzaldehyde, dissolved in 10 ml of water and 150 ml of methylcellosolve, are added to the filtrate. The reaction solution is stirred for 10 hours at 20° to 25° C. A little by-product is filtered off as a precipitate. The filtrate is concentrated to half its volume in vacuo and acetone is added until precipitation is complete. The precipitate is filtered off and dried in vacuo. 9.8 g of substance of the formula

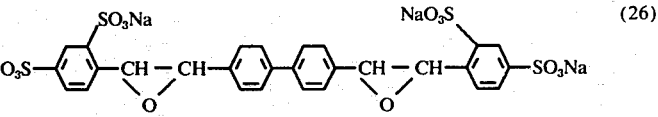

which still contains a little sodium chloride are obtained.

If instead of the di-Na salt of 2,4-disulphobenzaldehyde, the di-Na salt of 2,5-disulphobenzaldehyde is used, the compound of the formula

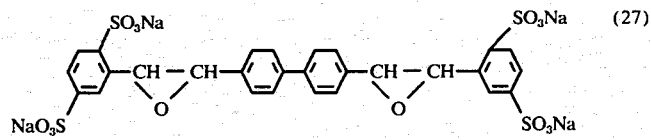

is obtained.

The compounds of the formulae (26) and (27) are reduced as described in Example 1 with thiourea to give the compounds of the formulae

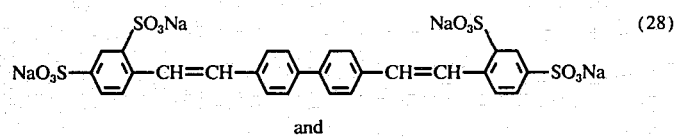

and

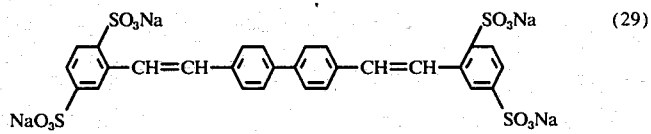

EXAMPLE 10

21.4 g of bis-sulphonium compound of the formula (2) are dissolved in 200 ml of methanol. 6 g of NaOH, dissolved in 10 ml of water, are added dropwise at −10° C. The resulting sodium chloride is filtered off at −10° C. 19 g of 2-phenyl-v-triazolyl-4-aldehyde are added to the filtrate. The suspension is first stirred for 2 hours at room temperature and then for 3 hours at 60° C. After cooling to 20° C, the precipitate is filtered off and dried in vacuo at 40° C. 22.7 g (86.6% of theory) of a light yellow powder of the formula

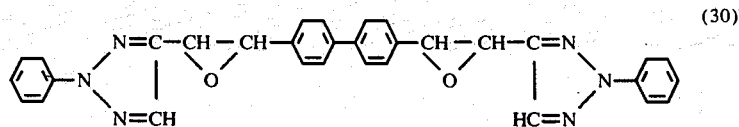

of melting point 158° to 159° C are obtained.

5 g of bis-epoxide of the formula (30) are dissolved in 150 ml of dimethylformamide and 40 ml of methanol. After adding 10 g of thiourea, the mixture is warmed to 60° – 70° C for 15 hours. A light yellow precipitate forms on addition of 60 ml of methanol and subsequent cooling to 0° C. This is filtered off and rinsed with a little methanol. After drying, 2.5 g (53% of theory) of a substance of the formula

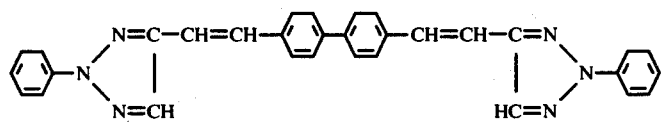

(31)

of melting point 260° C are obtained.

EXAMPLE 11

5 g of bis-epoxide of the formula (30) are dissolved in 150 ml of dimethylformamide. 10 g of Zn dust and 1 ml of 2 N NaOH are added. The mixture is warmed to 70° C and 10 ml of water are added. After stirring for 20 hours at 70° C, the Zn sludge is filtered off and eluted with hot dimethylformamide. An equal volume of methanol is added to the filtrate and the mixture is cooled to 0° C. The precipitate is filtered off and dried in vacuo. 1.6 g (34% of theory) of a pale yellow powder of the formula (31) and of melting point 260° C are thus obtained.

In a second aspect, the present invention relates to a new process for the manufacture of sulphonium salts, the new sulphonium salts obtainable therewith and their use for the manufacture of dyestuff salts which can be applied from organic solvents.

The most frequently used method for the manufacture of sulphonium salts consists of the alkylation of thio ethers in a non-acid medium. In many cases, however, the corresponding yields were relatively low and no reaction whatsoever took place. It was also frequently necessary to use the expensive alkyl iodides, which are difficult of access but are more reactive, as alkylating agents (compare U.S. Pat. No. 2,794,026, U.S. Pat. No. 3,078,259 and U.S. Pat. No. 3,455,967).

The process according to the invention now permits, economically and in good yields, the manufacture of new sulphonium salts of the formula

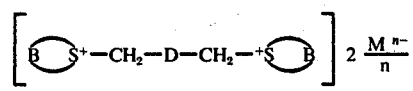

(I)

wherein the two B's independently of one another represent a polymethylene ring with 4 to 7 methylene groups which is optionally interrupted by a further hetero-atom and can be substituted by alkyl groups with 1 to 4 carbon atoms, D denotes the 4,4'-diphenylylene radical or a 1,5- or 2,6-naphthylene radical or a 9,10-dihydrophenanthrene or dibenzofurane radical which is bonded to the —CH$_2$— groups in the 2,7-position, M denotes an anion, especially the anion of an inorganic acid and $n$ denotes the number 1 or 2, in that compounds of the formula II

X—CH$_2$—D—CH$_2$—X    (II)

wherein X denotes a halogen atom, especially chlorine or bromine, or a $$-O-\overset{\overset{O}{\|}}{C}-X_1$$

group, wherein X$_1$ represents an aliphatic, cycloaliphatic or aromatic hydrocarbon radical, especially an alkyl radical with 1 to 6 carbon atoms or the phenyl radical, and D has the indicated meaning, are reacted in a strongly acid medium, in a molar ratio of at least 1:2, with organic sulphides of the formula III

    (III)

wherein B has the abovementioned meaning.

Preferred sulphonium salts are those of the formula I wherein both B's are identical and each together with the S atom form a tetrahydrothiophene, thiane, thiepane or 1,4-oxathiane ring, D denotes the 4,4'-diphenylylene radical and M and $n$ have the meaning indicated under the formula I, and very especially sulphonium salts of the formula Ia

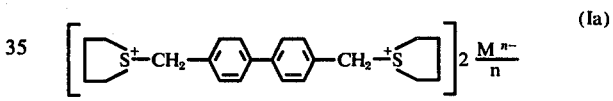

(Ia)

in which M denote an anion, especially an anion of hydrochloric acid or sulphuric acid and n denotes the number 1 or 2.

As examples of compounds of the formula II which can be employed in the process according to the invention, there may be mentioned: 4,4'-bis-(chloromethyl)-diphenyl, 4,4'-bis-(bromomethyl)-diphenyl, 4,4'-bis-(hydroxymethyl)-diphenyl diacetate, 1,5- or 2,6-bis-(chloromethyl)-naphthalene, 1,5- or 2,6-bis-(bromomethyl)-naphthalene, 2,7-bis-(chloromethyl)-9,10-dihydrophenanthrene and 2,7-bis-(bromomethyl)-dibenzofurane.

Preferably, compounds of the formula II are used in which X represents chlorine or bromine and D represents the 4,4'-diphenylylene radical.

Examples of organic sulphides of the formula III are: tetrahydrothiophene, 2- or 3-methyl-tetrahydrothiophene, 3-ethyl-tetrahydrothiophene, 2,4-dimethyl-tetrahydrothiophene, 2,3-dimethyl-tetrahydrothiophene, thiane, thiepane, 1,3- or 1,4-dithiane and 1,4-oxathiane.

Although mixtures of organic sulphides of the formula III can also be employed in the process according to the invention, preferably at least 2 mols of a sulphide of the formula III are used, in which B together with the S atom forms a tetrahydrothiophene, thiane, thiepane or 1,4-oxathiane ring.

The compounds which can be used as starting substances according to the invention are known or can be manufactured according to known methods.

The reaction of the reactants in a strongly acid medium is appropriately carried out at temperatures of about 10° C to 100° C, preferably at 40° C to 70° C.

The strongly acid medium used advantageously consists of inorganic acids, especially hydrochloric, hydrobromic, hydrofluoric, perchloric, sulphuric or phosphoric acid. These acids are preferably employed in an aqueous form; however, it is also possible to use solutions of anhydrous inorganic acids in organic solvents which are inert under the reaction conditions, for example lower aliphatic alcohols, such as methanol and ethanol, acetic acid, propionic acid, acetic anhydride, sulpholane, dioxane, nitromethane, benzene, chlorobenzene, nitrobenzene or nitrotoluene or a mixture of such solvents. A particularly preferred strongly acid medium is aqueous sulphuric acid, especially a 60 – 80% aqueous sulphuric acid, or aqueous hydrochloric acid, especially a 35 – 38% strength aqueous hydrochloric acid.

According to the definition, the compounds of the formula II and the organic sulphides of the formula III are employed in a molar ratio of at least 1:2; however, it is advisable to use an approximately 5 – 30% excess of organic sulphide.

The acid must also be present in at least equivalent amounts; preferably, however, an excess of acid is used.

In practice, the reaction according to the invention can be carried out by mixing the compound of the formula II with the organic sulphide of the formula III and introducing the mixture into the acid medium. It is, however, also possible first to introduce the compound of the formula II into an acid medium and to add the organic sulphide subsequently or, finally, it is preferentially possible first to introduce the organic sulphide into the acid medium and then to add the compound of the formula II. The reaction time is in general 1 to 50 hours, depending on the reactivity of the components.

The isolation and working-up of the sulphonium salts of the formula I can be carried out in various ways depending on the reaction medium and on the solubility properties of the end product. If volatile inorganic acids, such as hydrochloric acid, are used, the reaction product can be separated off directly, especially when working in an anhydrous medium, or can be isolated, for example, by evaporation under reduced pressure. The sulphonium salts can also be precipitated by dilution of the acid aqueous reaction medium with a suitable water-miscible organic solvent in which the sulphonium salt is insoluble, such as acetone, and be filtered off subsequently. Finally, in the case of the reaction in aqueous sulphuric acid or aqueous phosphoric acid, the reaction medium can be diluted with ice water and then neutralised with calcium hydroxide; after separating off the calcium sulphate or calcium phosphate which has separated out, the aqueous solution is evaporated in vacuo.

The sulphonium salts manufactured according to the new process are solid substances, in accordance with their salt character. At elevated temperatures they melt in part at an ill-defined temperature, with decomposition. They are characterised, for example, as the halide, especially chloride, and also as the bisulphate, sulphate, perchlorate, thiocyanate, picrate or picrylsulphonate, but in particular as the Reineckate, because of their low solubility. Most of the sulphonium salts are very easily water-soluble in the form of their halides and sulphates; frequently, however, they also dissolve in organic solvents such as ethanol or chloroform.

The sulphonium salts obtainable according to the invention can be used for the manufacture of water-insoluble salts of anionic dyestuffs which can be applied from organic solvents. Such dyestuff salts are suitable for dyeing organic fibre material, especially fibre material of synthetic polyamides, such as polycondensation products of hexamethylenediamine and adipic acid (polyamide 6,6) or sebacic acid (polyamide 6,10) or the polyaddition products of ε-caprolactam known under the trade names "Nylon 6", "Perlon", "Grilon" or "Enkalon", and the like, from organic solvents or solvent mixtures, optionally with the addition of a little water, for example from non-polar aprotic organic solvents optionally containing a little water, or their mixtures with polar organic solvents, such as tetrachloroethylene or mixtures of tetrachloroethylene or trichloroethylene, a little water and glacial acetic acid, methanol or dimethylacetamide.

The dyestuff salts can be manufactured in a manner which is in itself known, for example by double decomposition, by reacting an alkali metal salt or ammonium salt of an anionic dyestuff with a sulphonium salt according to the invention. The dyestuff salts can also be manufactured in situ, that is to say in the solvent or solvent mixture itself, from an alkali metal salt or ammonium salt of an anionic dyestuff and the sulphonium salt.

The process according to the invention permits the manufacture of hitherto inaccessible sulphonium salts, inter alia also from carboxylic acid esters which previously could not be reacted with thio ethers according to the known processes. In spite of the strongly acid conditions, practically no by-products are formed, so that the yields are in most cases very high.

The sulphonium salts according to the invention are also accessible, for example, by treatment of compounds of the formula II in which X denotes a hydroxyl group, if the reaction with the sulphide is carried out in a strongly acid medium, or from the appropriate sulphonic acid esters in a neutral medium.

The examples which follow illustrate the invention.

EXAMPLE 12

25.1 g of 4,4'-bis-(chloromethyl)-diphenyl and 21.2 g of tetrahydrothiophene are introduced into 25 ml of 37% strength aqueous hydrochloric acid. The reaction mixture is kept for 4 hours at a temperature of 65° C whilst stirring and is subsequently cooled to approx. 20° C and mixed with 250 ml of acetone. The reaction product is then caused to crystallise by means of ice cooling, filtered off and dried in vacuo at room temperature (approx. 25° C). 50.2 g of a white crystalline chromatographically pure product of the formula

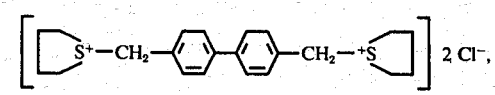

are obtained, which still contains solvent of crystallisation and has a melting point of 104°–105° C. Taking into account the analytically determined content, a yield of 98% of theory is found.

The content is determined by precipitating an aliquot part of the sulphonium salt with an aqueous solution of Reinecke salt. The resulting sparingly soluble Reineckate of melting point 185° C is dried and weighed.

Instead of isolating the end product by dilution of the reaction mixture with acetone, it is also possible to work up the reaction mixture by distilling off the hydrochloric acid and the excess tetrahydrothiophene under reduced pressure.

If in the above example, using otherwise the same procedure, 25 ml of 37% strength aqueous hydrochloric acid are replaced by the corresponding volume of waer, 36% of theory of a non-crystalline smeary mixture consisting of mono- and bis-sulphonium compound are obtained.

The table which follows lists further sulphonium salts which have been manufactured according to the process described above. Herein Reineckate denotes: salt with the anion $[Cr(SCN)_4(NH_3)_2]^{(-)}$.

of melting point 191° to 194° C are obtained.

EXAMPLE 17

5.7 g of the dyestuff of the formula

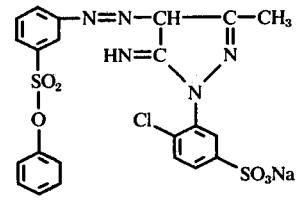

are dissolved in 200 ml of water. 2.15 g of the sulphonium salt of the formula

Table

| Example No. | Compound of the formula II | Sulphide | Reaction conditions hrs/° C | Acid medium | Sulphonium salt | Yield, % of theory (chloride) | Melting point |
|---|---|---|---|---|---|---|---|
| 13 | ClCH₂—⬡—⬡—CH₂Cl | S (tetrahydrothiophene) | 9 hrs/60° C | Aqueous 35% strength HCl | [⬡—S⁺—CH₂—⬡—⬡—CH₂—⁺S—⬡] 2 Cl⁻ | 95% | Reineckate 197° C (decomposition) |
| 14 | " | S (thiane) | 16 hrs/60° C | " | [⬡—S⁺—CH₂—⬡—⬡—CH₂—⁺S—⬡] 2 Cl⁻ | 55% | Reineckate 163° C (decomposition) |
| 15 | " | S—O (thioxane) | 24 hrs/60° C | " | [O⬡S⁺—CH₂—⬡—⬡—CH₂—⁺S⬡O] 2 Cl⁻ | 58% | Reineckate 161° C (decomposition) |

EXAMPLE 16

15.9 g of 2,7-bis-(bromomethyl)-dibenzofurane and 11.9 g of tetrahydrothiophene are introduced into 60 ml of 37% strength hydrochloric acid. The reaction mixture is stirred for 6 hours at 60° C. The hydrochloric acid is evaporated off in vacuo and the residue is taken up in a little ethanol. Hereupon, crystallisation immediately occurs and is completed by cooling with ice. The product is filtered off and dried in vacuo at room temperature. 19.8 g (83% of theory) of the white, chromatographically pure product of the formula

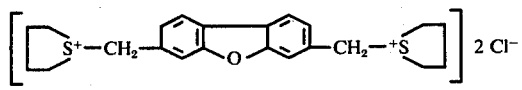

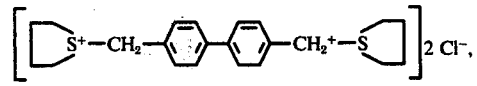

dissolved in 50 ml of water are added to the resulting solution, whilst stirring. Thereafter, the resulting precipitate is filtered off and dried in vacuo at 50° C. 6.5 g of the dyestuff salt of the formula

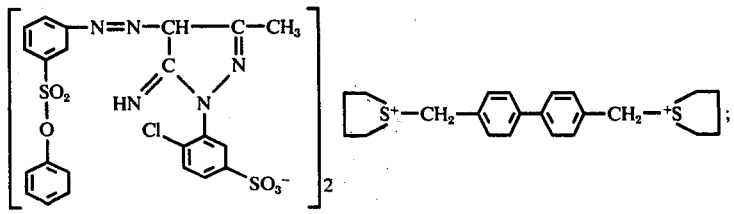

are obtained, melting point 144° – 147° C (decomposition).

The above dyestuff salt can, for example, be used as follows for dyeing synthetic polyamide:

100 g of polyamide-6,6 knitted fabric are introduced, at room temperature (approx. 25° C), into a dyebath (liquor ratio 1:10) which was obtained by mixing 1 g of the finely ground dyestuff salt of the above formula, 0.5 ml of glacial acetic acid and 40 ml of water with 960 ml of tetrachloroethylene. The dyebath is subsequently warmed to 121° C in a closed system, with constant agitation of the material being dyed, and is kept at this temperature for 60 minutes. After cooling the dyebath, the knitted fabric is rinsed with acetone at room temperature and subsequently dried. A strongly coloured yellow dyeing of good evenness is obtained.

1. In a process for the manufacture of compounds of the formula

wherein A and $A_1$ independently of one another denote phenyl, naphthyl, diphenylyl, 2-phenyl-1,2,3-triazol-4-yl or pyridyl, it being possible for A and $A_1$ to contain non-chromophoric substituents, and D denotes the 4,4'-diphenylylene radical, 1,5- or 2,6-naphthylene radical or a 9,10-dihydrophenanthrene or dibenzofurane radical which is bonded to the ethylene groups in the 2,7-position, characterised in that in a first stage a compound of the formula

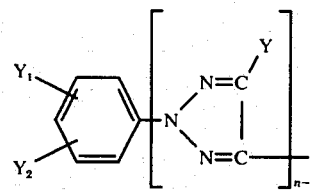

X — $CH_2$ — D — $CH_2$— X         (II)

wherein X denotes a halogen atom, especially chlorine or bromine, the hydroxyl group or a group

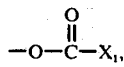

wherein $X_1$ represents an aliphatic, cycloaliphatic or aromatic hydrocarbon radical, especially an alkyl radical with 1 to 6 carbon atoms, or the phenyl radical and D has the indicated meaning, the improvement wherein the compound of formula (II) is reacted in a strongly acid medium at a temperature of about −20° C to 120° C, in a molar ratio of at least 1:2, with an organic sulphide containing 5 to 8 ring members, of the formula

         (III)

wherein B represents a polymethylene group of 4 to 7 methylene groups and wherein one of these methylene groups can be replaced by a hetero-atom and wherein these methylene groups can also contain alkyl groups with 1 to 4 carbon atoms as substituents, to give a sulphonium salt of the formula

         (IV)

wherein M represents the anion of the strong acid used and n denotes the numbers 1 or 2; that, further, in a second stage the resulting sulphonium salt is mixed at temperatures below 20° C with 2 mols of an aldehyde of the formula

A-CHO         (V)

or $A_1$-CHO         (VI)

of their mixture, in the presence of strong bases, in a strongly polar, protic or aprotic, water-miscible solvent then reacted at a temperature up to the boiling point of the solvent to give a diepoxide of the formula

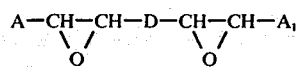

and that the diepoxide of the formula (VII), thus obtained, is subjected, in a 3rd stage, to an epoxide reduction process at a temperature between 40° and 80° C with elimination of the epoxide oxygen and formation of ethylene groups.

2. Process according to claim 1 for the manufacture of compounds of the formula

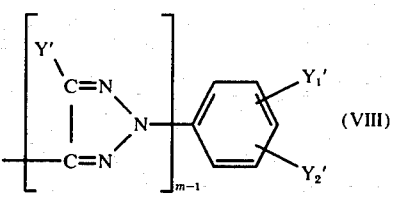

wherein Y and Y' independently of one another denote hydrogen or methyl, $Y_1$ and $Y_1'$ independently of one another denote hydrogen, the sulphonic acid group or its Na, K or ammonium salt, carbomethoxy, nitrile or methoxy, $Y_2$ and $Y_2'$ independently of one another denote hydrogen, chlorine, methyl or the sulphonic acid group or its Na, K or ammonium salt, n and m independently of one another denote the number 1 or 2 and D denotes the 4,4'-diphenylylene radical, the 1,5- or 2,6-naphthylene radical or a 9,10-dihydrophenanthrene or dibenzofurane radical which is bonded to the ethylene groups in the 2,7-position, characterised in that in the first process stage a compound of the formula $X_2$ — $CH_2$ — D — $CH_2$ — $X_2$         (XI)

wherein $X_2$ represents chlorine or bromine, is employed, and the sulphonium salt obtained therefrom is reacted, in the second process stage, with an aldehyde of the formula

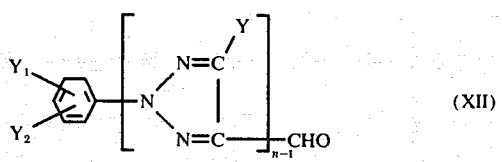

and/or

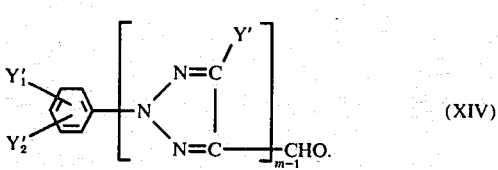

3. Process according to claim 1 for the manufacture of stilbene derivatives of the formula

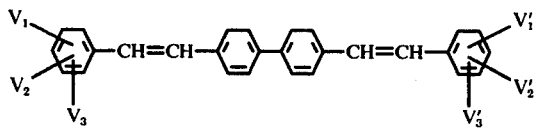

wherein $V_1$ and $V_1'$ independently of one another denote hydrogen, a sulphonic acid group as well as its salts, esters or amides, a carboxylic acid group as well as its salts, esters or amides, the nitrile group, a sulphone group or a methyl group, $V_2$ and $V_2'$ independently of one another denote hydrogen, an alkyl group containing 1 to 18 carbon atoms, an alkoxy group containing 1 to 12 carbon atoms, halogen or a sulphonic acid group, as well as its salts, esters or amides and $V_3$ and $V_3'$ independently of one another denote hydrogen, halogen or an alkyl group containing 1 to 4 carbon atoms, characterised in that in the first process stage a compound of the formula

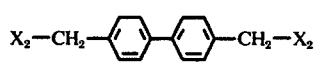 (XII)

wherein $X_2$ represents chlorine or bromine, is employed, and the sulphonium salt obtained therefrom is reacted, in the second process stage, with an aldehyde

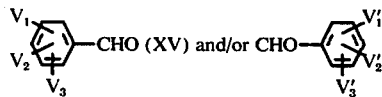 (XVI)

4. Process according to claim 1 for the manufacture of stilbene derivatives of the formula

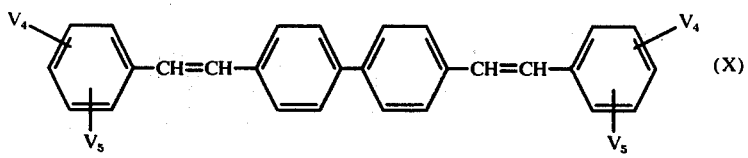 (X)

wherein $V_4$ denotes hydrogen, a sulphonic acid group as well as its salts, esters or amides, a carboxylic acid group as well as its salts, esters or amides, halogen or the nitrile group and $V_5$ denotes hydrogen, halogen, a sulphonic acid group as well as its salts, esters or amides, an alkyl group with 1 to 4 carbon atoms or an alkoxy group with 1 to 4 carbon atoms, characterised in that in the first process stage a compound of the formula

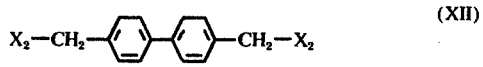 (XII)

wherein $X_2$ represents chlorine or bromine, is employed, and the sulphonium salt manufactured therefrom is reacted, in the second process stage, with about 2 mols of an aldehyde of the formula

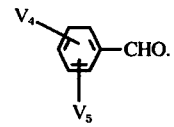 (XVII)

5. Process according to claim 1 for the manufacture of 4,4'-di-(2-sulphostyryl)-biphenyl, characterised in that in the first stage a compound of the formula

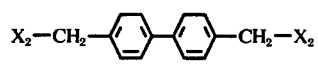 (XII)

wherein $X_2$ represents chlorine or bromine, is reacted with tetrahydrothiophene, and the sulphonium salt thus obtained is reacted, in the second stage, with about 2 mols of benzaldehyde-o-sulphonic acid and the resulting diepoxide is reduced in the third stage.

6. Process according to claim 1, characterised by the use of a sulphide of the formula (III), wherein B together with the sulphur atom forms a thiacycloheptane, a 1,4-oxathiacyclohexane, a thiacyclohexane or preferably a tetrahydrothiophene ring.

7. Process according to claim 1, characterised in that the reaction of the 1st stage is carried out in the presence of an inorganic acid which has a pK value of less than 4.5 in an aqueous medium, preferably hydrochloric acid or sulphuric acid.

8. Process according to claim 1, characterised in that in the reaction in the second stage the sulphonium salt dissolved in a lower primary aliphatic alcohol, preferably methanol, or in a mixture of the alcohol with water, is treated, at temperatures of −5 to −20° C, first with NaOH or KOH and then with the aldehyde or aldehyde mixture, and the reaction mixture is subsequently heated to a temperature between 40° C and the boiling point of the solvent.

9. Process according to claim 1, characterised in that in the third stage the reduction is carried out by means of thiourea.

10. Process according to claim 1, characterised in that in the third stage the reduction is carried out by means of zinc and alkali metal hydroxide or zinc and acid.

11. Process according to claim 1, characterised in that in the third stage the reduction is carried out catalytically with hydrogen.

* * * * *